(12) United States Patent
Varadhan et al.

(10) Patent No.: US 11,857,185 B2
(45) Date of Patent: Jan. 2, 2024

(54) SURGICAL STAPLING DEVICE WITH SHIPPING CAP

(71) Applicant: Covidien LP, Mansfield, MA (US)

(72) Inventors: Sridharan Varadhan, Shanghai (CN); Zhinan Guo, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/787,264

(22) PCT Filed: Dec. 18, 2019

(86) PCT No.: PCT/CN2019/126252
§ 371 (c)(1),
(2) Date: Jun. 18, 2022

(87) PCT Pub. No.: WO2021/120046
PCT Pub. Date: Jun. 24, 2021

(65) Prior Publication Data
US 2023/0049244 A1 Feb. 16, 2023

(51) Int. Cl.
*A61B 17/072* (2006.01)
*A61B 90/00* (2016.01)

(52) U.S. Cl.
CPC ............ *A61B 17/072* (2013.01); *A61B 90/03* (2016.02); *A61B 2017/07271* (2013.01); *A61B 2090/038* (2016.02)

(58) Field of Classification Search
CPC ........ A61B 17/072; A61B 2017/07271; A61B 2090/038; A61B 90/03; A61B 2090/034; A61B 2017/07214

(Continued)

(56) References Cited

U.S. PATENT DOCUMENTS 1,158,111 A 10/1915 Ahlheim
2,891,250 A 6/1959 Hirata
(Continued)

FOREIGN PATENT DOCUMENTS

CN 202173422 U 3/2012
CN 104027141 A 9/2014
(Continued)

OTHER PUBLICATIONS

International Search Report issued in corresponding International Application No. PCT/CN2019/126252 dated Sep. 27, 2020, 11 pages.
(Continued)

*Primary Examiner* — Valentin Neacsu
(74) *Attorney, Agent, or Firm* — Carter, DeLuca & Farrell LLP (57) ABSTRACT

A surgical stapling device (10) includes a reload assembly (300) having a cartridge assembly (100) and a shipping cap (200) releasably attached to the cartridge assembly (100). The cartridge assembly (100) includes an alignment pin assembly (140) having an alignment pin (144) defining a key hole slot (151) and is movable between a locked position and an unlocked position. The shipping cap (200) includes a locking pin (230) received through the key hole slot (151). When the alignment pin (144) is in the locked position, the alignment pin (144) prevents separation of the shipping cap (200) from the replaceable cartridge assembly (100) and when the alignment pin (144) is in the unlocked position, the alignment pin (144) permits separation of the shipping cap (200) from the replaceable cartridge assembly (100).

17 Claims, 7 Drawing Sheets

(58) Field of Classification Search
USPC ..................................................... 227/175.2
See application file for complete search history.

(56) References Cited

U.S. PATENT DOCUMENTS

| | | | |
|---|---|---|---|
| 3,080,564 A | 3/1963 | Strekopitov et al. |
| 3,252,643 A | 5/1966 | Strekopov et al. |
| 3,269,630 A | 8/1966 | Fleischer |
| 3,275,211 A | 9/1966 | Hirsch et al. |
| 3,315,863 A | 4/1967 | D'Dea |
| 3,494,533 A | 2/1970 | Green et al. |
| 3,589,589 A | 6/1971 | Akopov |
| 3,692,224 A | 9/1972 | Astafiev et al. |
| 3,795,034 A | 3/1974 | Strekopytov et al. |
| 3,822,818 A | 7/1974 | Strekopytov et al. |
| 3,935,981 A | 2/1976 | Akopov et al. |
| 3,949,923 A | 4/1976 | Akopov et al. |
| 4,047,654 A | 9/1977 | Alvarado |
| 4,216,891 A | 8/1980 | Behlke |
| 4,244,372 A | 1/1981 | Kapitanov et al. |
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,571,285 A | 11/1996 | Chow et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 | 11/2004 | Racenet et al. |
| 6,988,650 B2 | 1/2006 | Schwemberger et al. |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,210,609 B2 | 5/2007 | Eiboff et al. |
| 7,237,708 B1 | 7/2007 | Guy et al. |
| 7,275,674 B2 | 10/2007 | Racenet et al. |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,828,188 B2 | 11/2010 | Jankowski |
| 7,886,953 B2 | 2/2011 | Schwemberger et al. |
| 8,016,176 B2 | 9/2011 | Kasvikis et al. |

(56) References Cited

U.S. PATENT DOCUMENTS

| | | |
|---|---|---|
| 8,029,520 B2 | 10/2011 | Korvick et al. |
| 8,033,439 B2 | 10/2011 | Racenet et al. |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,328,064 B2 | 12/2012 | Racenet et al. |
| 8,360,296 B2 | 1/2013 | Zingman |
| 8,418,906 B2 | 4/2013 | Farascioni et al. |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,936,185 B2 | 1/2015 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 9,192,387 B1 | 11/2015 | Holsten et al. |
| 9,480,474 B2 | 11/2016 | Ji et al. |
| 9,566,066 B2 | 2/2017 | Kasvikis |
| 9,579,102 B2 | 2/2017 | Holsten et al. |
| 9,655,619 B2 | 5/2017 | Zhang et al. |
| 9,662,111 B2 | 5/2017 | Holsten et al. |
| 9,668,736 B2 | 6/2017 | Holsten et al. |
| 9,675,349 B2 | 6/2017 | Holsten et al. |
| 9,675,350 B2 | 6/2017 | Holsten et al. |
| 9,675,356 B2 | 6/2017 | Racenet et al. |
| 9,814,460 B2 | 11/2017 | Kimsey et al. |
| 9,888,923 B2 | 2/2018 | Chen et al. |
| 9,962,159 B2 | 5/2018 | Heinrich et al. |
| 10,004,504 B2 | 6/2018 | Bryant |
| 10,085,754 B2 | 10/2018 | Sniffin et al. |
| 10,194,913 B2 | 2/2019 | Nalagatla et al. |
| 2004/0164123 A1 | 8/2004 | Racenet et al. |
| 2005/0143759 A1* | 6/2005 | Kelly ................ A61B 17/072 |
| | | 606/139 |
| 2005/0145672 A1 | 7/2005 | Schwemberger et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0187456 A1 | 8/2007 | Viola et al. |
| 2010/0048988 A1 | 2/2010 | Pastorelli et al. |
| 2011/0101066 A1* | 5/2011 | Farascioni ....... A61B 17/07207 |
| | | 227/175.2 |
| 2012/0234894 A1* | 9/2012 | Kostrzewski .... A61B 17/07207 |
| | | 206/363 |
| 2012/0267418 A1* | 10/2012 | Farascioni ............ A61B 90/00 |
| | | 227/175.3 |
| 2013/0206813 A1 | 8/2013 | Nalagatla |
| 2014/0252065 A1 | 9/2014 | Hessler et al. |
| 2016/0249914 A1 | 9/2016 | Zhang et al. |
| 2016/0249923 A1 | 9/2016 | Hodgkinson et al. |
| 2016/0270784 A1 | 9/2016 | Wheeler et al. |
| 2016/0270790 A1 | 9/2016 | Jankowski |
| 2016/0270793 A1 | 9/2016 | Carter et al. |
| 2016/0278779 A1 | 9/2016 | Jankowski |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0128149 A1 | 5/2017 | Heinrich et al. |
| 2017/0189021 A1 | 7/2017 | Kimsey et al. |
| 2017/0238923 A1 | 8/2017 | Holsten et al. |
| 2017/0238924 A1 | 8/2017 | Holsten et al. |
| 2017/0265861 A1 | 9/2017 | Holsten et al. |
| 2018/0008261 A1 | 1/2018 | Racenet et al. |
| 2018/0049739 A1 | 2/2018 | Kasvikis |
| 2018/0153544 A1 | 6/2018 | Maddur Shankarsetty et al. |
| 2018/0221024 A1 | 8/2018 | Heinrich et al. |
| 2023/0049244 A1* | 2/2023 | Varadhan ............. A61B 17/072 |

FOREIGN PATENT DOCUMENTS

| | | |
|---|---|---|
| CN | 104146739 A | 11/2014 |
| CN | 108652692 A | 10/2018 |
| CN | 208511104 U | 2/2019 |
| CN | 208973965 U | 6/2019 |
| CN | 209499804 U | 10/2019 |
| EP | 2499987 A2 | 9/2012 |
| JP | S493958 B1 | 1/1974 |
| JP | 2005514101 A | 5/2005 |
| JP | 2006320720 A | 11/2006 |
| JP | 2010508911 A | 3/2010 |
| JP | 2012196435 A | 10/2012 |
| JP | 2015119955 A | 7/2015 |
| JP | 2018500102 A | 1/2018 |
| JP | 2018518217 A | 7/2018 |

OTHER PUBLICATIONS

European Search Report dated Aug. 9, 2023, issued in corresponding European Appln. No. 19/956,746, 6 pages.

Japanese Office Action dated Sep. 8, 2023, issued in corresponding Japanese Appln. No. 2022532067, 16 pages.

* cited by examiner

SURGICAL STAPLING DEVICE WITH SHIPPING CAP

CROSS-REFERENCE TO RELATED APPLICATIONS

This application is a National Stage Application of PCT/CN2019/126252 filed Dec. 18, 2019, and the disclosure of the above-identified application is hereby incorporated by reference in its entirety.

FIELD

The technology is generally related to surgical stapling devices and, more particularly, to surgical stapling devices that include shipping caps.

BACKGROUND

Surgical stapling devices for applying rows of staples through compressed living tissue are known in the art and are commonly used for closure of tissue or organs prior to transection or resection of the tissue and for occlusion of the organs during thoracic or abdominal procedures. These stapling devices often include a cartridge or reload assembly that can be removed from the stapling device and replaced to facilitate reuse of the stapling device.

Typically, the stapling devices include a tool assembly having an anvil assembly and the replaceable cartridge assembly, a drive member for ejecting staples from the reload assembly, and an approximation assembly for moving the tool assembly between spaced and clamped positions. The replaceable cartridge assembly includes, inter alia, a staple pusher, a plurality of staples, and a body defining a plurality of staple pockets for receiving the staples. The pusher is movable within the body to eject the staples form the staple pockets.

Typically, cartridge assemblies are stored and shipped separately from the stapling device and are secured to the stapling device immediately prior to a surgical procedure. In order to maintain the pusher and the staples in their proper positions within the cartridge assembly during storage and shipping, it is common to have a shipping cap secured to the replaceable cartridge assembly. When the shipping cap is removed from the replaceable cartridge assembly prior to use, the potential for movement of the pusher and staples to positions that adversely affect proper operation of the stapling device increases.

SUMMARY

The aspects of this disclosure generally relate to a surgical stapling device including a replaceable cartridge assembly having a selectively releasable shipping cap. One aspect of the disclosure is directed to a stapling device including an elongate body portion defining a longitudinal axis, the elongate body portion having a distal portion, and an end effector supported on the distal portion of the elongated body portion. The end effector includes a housing having a base portion and a jaw portion, the base portion being secured to the distal portion of the elongate body portion, an anvil assembly supported on the jaw portion, a cartridge assembly releasably supported on the base portion, the cartridge assembly including an alignment pin assembly having an alignment pin, and a shipping cap releasably attached to the cartridge assembly. The alignment pin defines a key hole slot and is movable between a locked position and an unlocked position. The shipping cap includes a locking pin received through the key hole slot. When the alignment pin is in the locked position, the alignment pin prevents separation of the shipping cap from the replaceable cartridge assembly and when the alignment pin is in the unlocked position, the alignment pin permits separation of the shipping cap from the replaceable cartridge assembly.

In aspects of the disclosure, the key hole slot includes a first portion and a second portion, and the locking pin includes a shaft portion and a head portion, the shaft portion being received within the second portion of the key hole slot when the alignment pin is in the locked position and the shaft portion being received within the first portion of the key hole slot when the alignment pin is in the unlocked position. The first portion of the key hole slot may be rectangular and the second portion of the key hole slot may be circular. The head portion of the locking pin may engage the alignment pin when the alignment pin is in the locked position and may be free to pass through the alignment pin when the alignment pin is in the unlocked position.

In other aspects of the disclosure, the surgical stapling device includes a deployment member. Movement of the deployment member from a first position to a second position moves the alignment pin from the unlocked position to an advanced position in engagement with the anvil assembly. The surgical stapling device may include a body having a stationary handle and a trigger, wherein movement of the trigger towards the stationary handle causes the deployment member to move from the first position to the second position. The surgical stapling device may include at least one thumb button in operable engagement with the deployment member, wherein movement of the at least one thumb button moves the deployment member from the first position to the second position.

In some aspects of the disclosure, the shipping cap is in snap fit engagement with the cartridge assembly. The shipping cap may include a body portion and a staple retaining portion. The alignment pin assembly may include a spring for biasing the alignment pin to the locked position.

Another aspect of the disclosure is directed to a reload assembly including a cartridge assembly and a shipping cap releasably attached to the cartridge assembly. The cartridge assembly includes an alignment pin assembly having an alignment pin. The alignment pin defines a key hole slot and is movable between a locked position and an unlocked position. The shipping cap includes a locking pin received through the key hole slot. When the alignment pin is in the locked position, the alignment pin prevents separation of the shipping cap from the replaceable cartridge assembly and when the alignment pin is in the unlocked position, the alignment pin permits separation of the shipping cap from the replaceable cartridge assembly.

In other aspects of the disclosure, the key hole slot includes a first portion and a second portion, and the locking pin includes a shaft portion and a head portion. The shaft portion may be received within the second portion when the alignment pin is in the locked position and the shaft portion may be received within the first portion when the alignment pin is in the unlocked position. The first portion may be rectangular and the second portion may be circular. The head portion of the locking pin may engage the alignment pin when the alignment pin is in the locked position and may be free to pass through the alignment pin when the alignment pin is in the unlocked position.

In some aspects of the disclosure, the shipping cap is in snap fit engagement with the cartridge assembly. The shipping cap may include a body portion and a staple retaining portion. The alignment pin assembly may include a spring for biasing the alignment pin to the locked position.

Other features of the disclosure will be appreciated from the following description.

BRIEF DESCRIPTION OF DRAWINGS

Various aspects of the disclosure are described herein below with reference to the drawings, wherein.

DETAILED DESCRIPTION

The disclosed stapling devices will now be described in detail with reference to the drawings in which like reference numerals designate identical or corresponding elements in each of the several views. However, it is to be understood that the disclosed aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, and support personnel.

The disclosed surgical stapling device includes a reload assembly having a cartridge assembly and a shipping cap. As will be described in detail below, the shipping cap is configured to remain secured to the replaceable cartridge assembly until the reload assembly is properly installed on the surgical stapling device.

Figure 1:
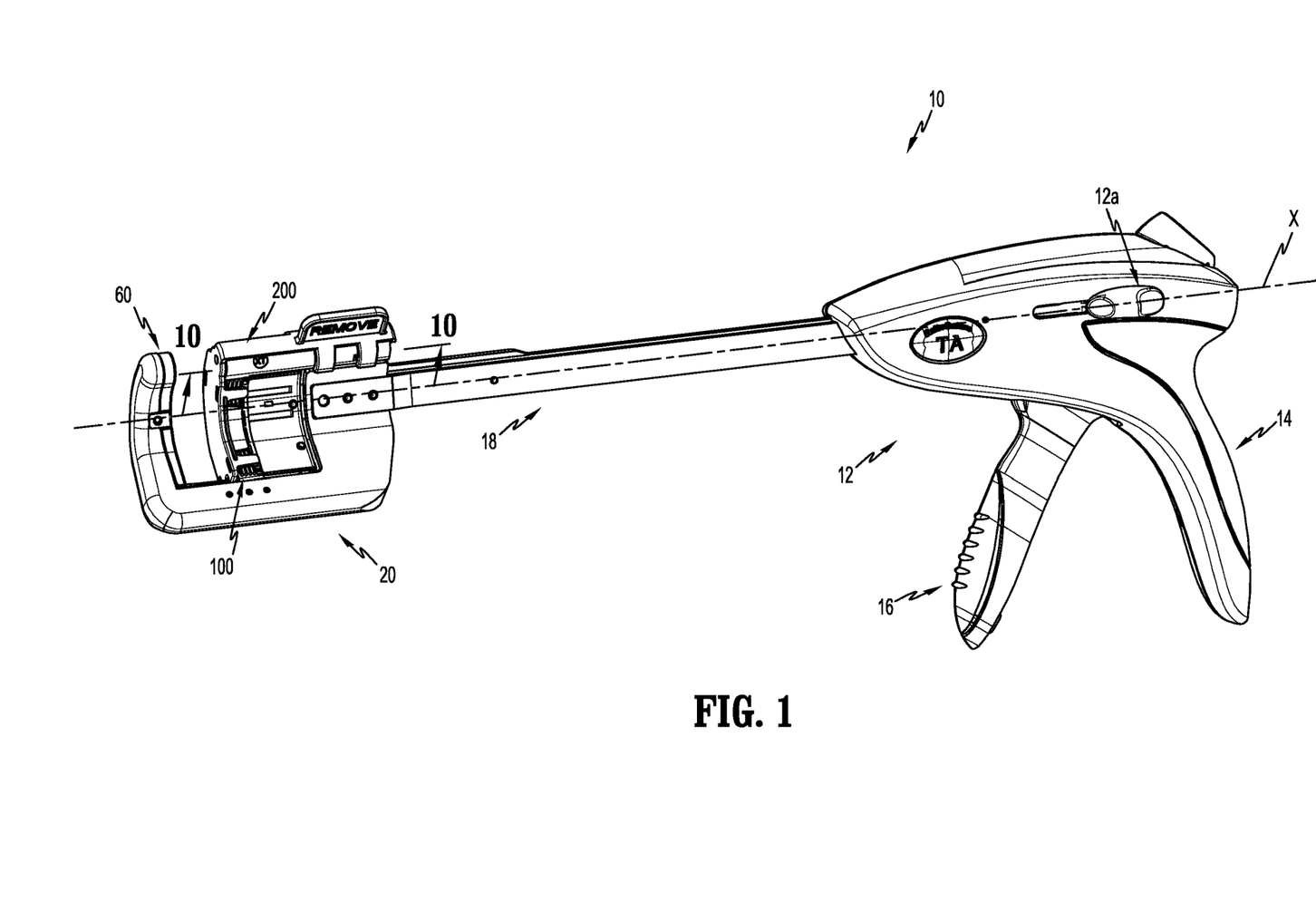
FIG. 1 is a side perspective view of a surgical stapling device according to the disclosure including an end effector supporting a replaceable cartridge assembly with the end effector in an open position and a shipping cap attached to the replaceable cartridge assembly.

FIG. 1 illustrates the disclosed surgical stapling device shown generally as stapling device 10. The stapling device 10 defines a longitudinal axis "X" and includes a body 12 defining a stationary handle 14, a pivotable trigger 16 that is movable relative to the stationary handle 14, an elongated central body portion 18 extending from the body 12, clamp slide members 30, and an end effector 20 that is disposed on a distal end of the elongated central body portion 18. The end effector 20 of the stapling device 10 includes an anvil assembly 60 and a replaceable cartridge assembly 100. A shipping cap 200 is releasably attached to the replaceable cartridge assembly 100 to maintain the replaceable cartridge assembly 100 in operable condition during storage and shipping. A thumb button 12a is slidably positioned on each side of the body 12 of the stapling device 10. The thumb buttons 12a (only one shown) are movable to manually advance an alignment pin 144 (FIG. 6) of an alignment pin assembly 140 (FIG. 3) of the replaceable cartridge assembly 100.

The stapling device 10 will be described to the extent necessary to fully disclose the aspects of the disclosure. For a detailed description of the internal structure and function of an exemplary surgical stapling device, please refer to commonly owned U.S. Pat. No. 6,817,508 ("the '508 patent"), and commonly owned U.S. Pat App. Pub. No. 2018/0153544 ("the '544 publication").

Figure 2:
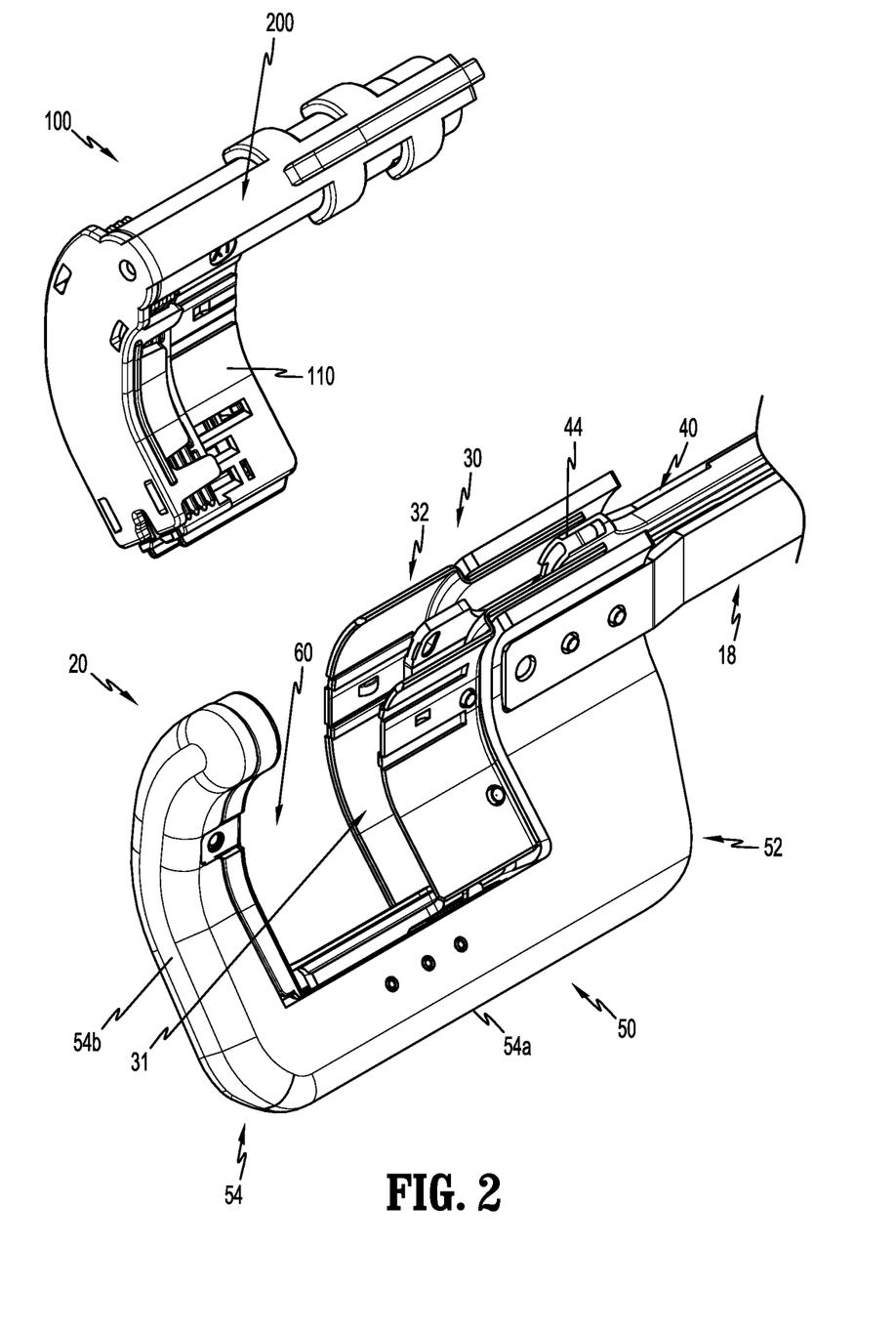
FIG. 2 is a perspective view of the end effector of the surgical stapling device shown in FIG. 1 with the replaceable cartridge assembly, including the attached shipping member, removed from the end effector.

FIG. 2 illustrates a distal portion of a frame 50 of the end effector 20 of the stapling device 10 (FIG. 1). The distal portion of the frame 50 includes a base portion 52 and an L-shaped jaw portion 54 extending from the base portion 52. The L-shaped jaw portion 54 includes a longitudinal portion 54a and a transverse portion 54b. The anvil assembly 60 is supported on the transverse portion 54b of the jaw portion 54 of the frame assembly 50 and the replaceable cartridge assembly 100 is releasably supported within a head portion 32 defined by the clamp slide members 30 which are movably supported within the base portion 52 of the frame assembly 50.

The base portion 52 and the transverse portion 54b of the jaw portion 54 of the frame assembly 50 of the end effector 20 are curved along an axis transverse to the longitudinal axis "X" of the stapling device 10. For example, the end effector 20 may be C-shaped or include a first radius of curvature and a second radius of curvature. The first and second radii of curvature may be increased or decreased to suit a particular procedure and/or to facilitate access to a particular body cavity or location within a body cavity. The end effector 20 may also be formed by a plurality of substantially linear sections that are connected to each other to define a curved-like configuration. Alternatively, the base portion 52 and the transverse portion 54b of the jaw portion 54 of the frame assembly 50 of the end effector 20 can have linear configurations. Each of the anvil assembly 60 and the replaceable cartridge assembly 100 include a configuration corresponding to the configuration of the frame assembly 50 of the end effector 20.

With continued reference to FIG. 2, the head portion 32 defined by the clamp slide members 30 of stapling device 10 support the replaceable cartridge assembly 100 and is slidably supported within the base portion 52 of the frame assembly 50 of the end effector 20. As disclosed in the '544 publication, the clamp slide members 30 advance in response to actuation of the trigger 16 (FIG. 1) of the stapling device 10 (FIG. 1) to cause advancement of the replaceable cartridge assembly 100 relative to the anvil assembly 60. The head portion 32 of the clamp slide members 30 define a channel 31 that is configured to releasably support the replaceable cartridge assembly 100. For a detailed description of the structure and operation of an exemplary end effector, please refer to the '544 publication.

An alignment pin pusher or deployment member 40 is slidably supported within the elongated central body portion 18 of the stapling device 10. The deployment member 40 has a distal end including an abutment member 44 that is positioned to engage with the alignment pin 144 of the alignment pin assembly 140 of the replaceable cartridge assembly 100 when the replaceable cartridge assembly 100 is supported on the end effector 20. The deployment member 40 is operable to advance and retract the alignment pin 144 of the alignment pin assembly 140. More specifically, the deployment member 40 is movable in response to movement of trigger 16 during an approximation stroke of the stapling device 10 to advance the alignment pin 144 of the alignment pin assembly 140 from a position within the replaceable cartridge assembly 100 into engagement with the anvil assembly 60. Alternatively, the deployment member 40 can be manually advanced using the thumb buttons 12a into engagement with the anvil assembly 60 prior to actuation of the trigger 16. The deployment member 40 will only be described to the extent necessary to fully disclose the aspects of the disclosure. For a detailed description of an exemplary deployment member, please refer to the '508 patent.

The deployment member 40 of the stapling device 10 includes a vertical portion 42 (FIG. 10) that supports the abutment member 44 (FIG. 2). The abutment member 44 is configured to engage a base member 142 of the alignment pin assembly 140 of the replaceable cartridge assembly 100 such that when the deployment member 40 is advanced, the alignment pin 144 is advanced from within cartridge 100 into an opening (not shown) of the anvil assembly 60.

Figure 3:
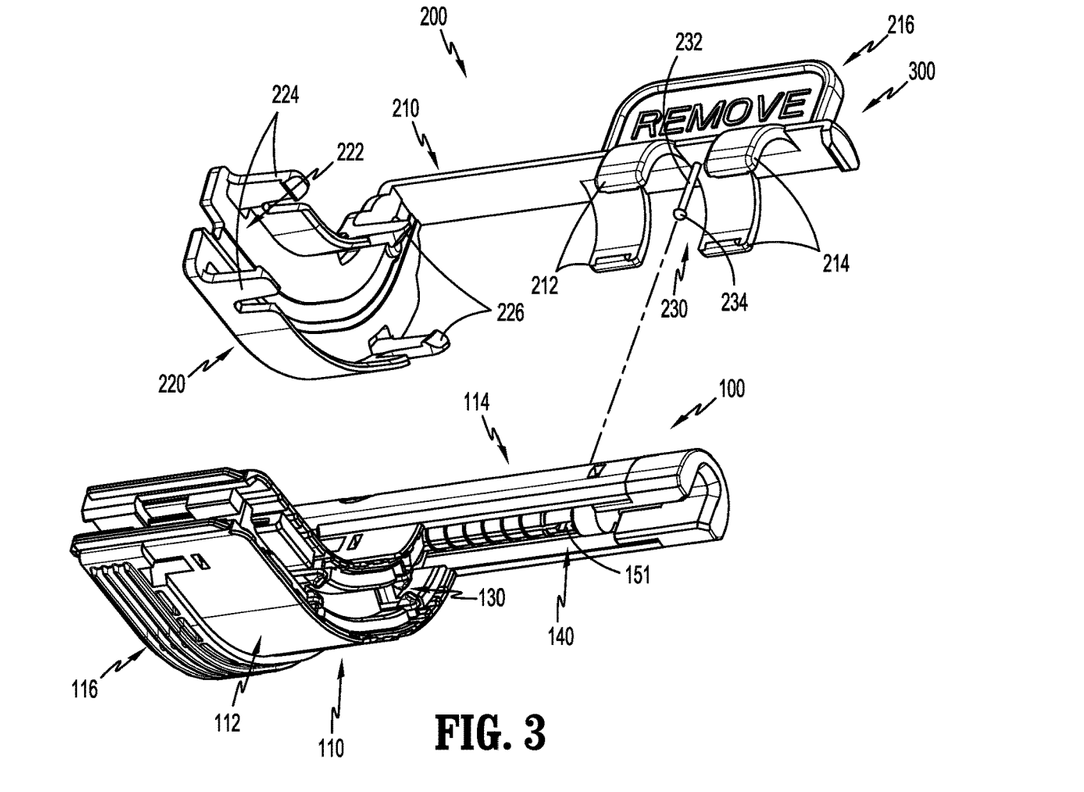
FIG. 3 is a bottom perspective view of the replaceable cartridge assembly and shipping cap shown in FIG. 1 with the shipping cap separated from the replaceable cartridge assembly.

FIG. 3 illustrates the replaceable cartridge assembly 100 and the shipping cap 200 separated from the replaceable cartridge assembly 100. The replaceable cartridge assembly 100 and the shipping cap 200 together form a reload assembly 300. The replaceable cartridge assembly 100 of the stapling device 10 includes a housing 110 having a base portion 112 and an alignment pin retaining portion 114 connected to the base portion 112. The base portion 112 supports a staple cartridge 116. A pusher assembly 130 is operably supported within the base portion 112, and the alignment pin assembly 140 is operably supported within the alignment pin retaining portion 114.

The shipping cap 200 includes a body portion 210, and a staple retaining portion 220 extending perpendicular from the body portion 210. The body portion 210 of the shipping cap 200 is configured to releasably engage the alignment pin retaining portion 114 of the housing 110 of the replaceable cartridge assembly 100. More particularly, the body portion 210 includes first and second pairs of resilient arms 212, 214 configured to be frictionally received about the alignment pin retaining portion 114 of the housing 110 of the replaceable cartridge assembly 100, thereby creating a snap fit engagement with between the shipping cap 200 and the replaceable cartridge assembly 100. Each arm of the first and second pairs of resilient arms 212, 214 may be longitudinal offset from the other, as shown. A handle or grip portion 216 extends outwardly from the body portion 210 in a direction opposite to the resilient arms 212, 214 and is configured for operable engagement by a user to facilitate separation of the shipping cap 200 from the replaceable loading unit 100. A locking pin 230 extends from the body portion 210 opposite the handle portion 216. As shown, the locking pin 230 is disposed between the first and second pairs of resilient arms 212, 214. The locking pin 230 includes a shaft portion 232 and a head portion 234 disposed on a free end of the shaft portion 232. The head portion 234 of the locking pin 230 includes a diameter that is larger than a diameter of the shaft portion 232. As will be described below, the locking pin 230 is configured to be selectively engaged by the alignment pin assembly 140 to selectively lock the shipping cap 200 to the replaceable cartridge assembly 100 to prevent premature separation of the shipping cap 200 from the replaceable cartridge assembly 100.

Figure 4:
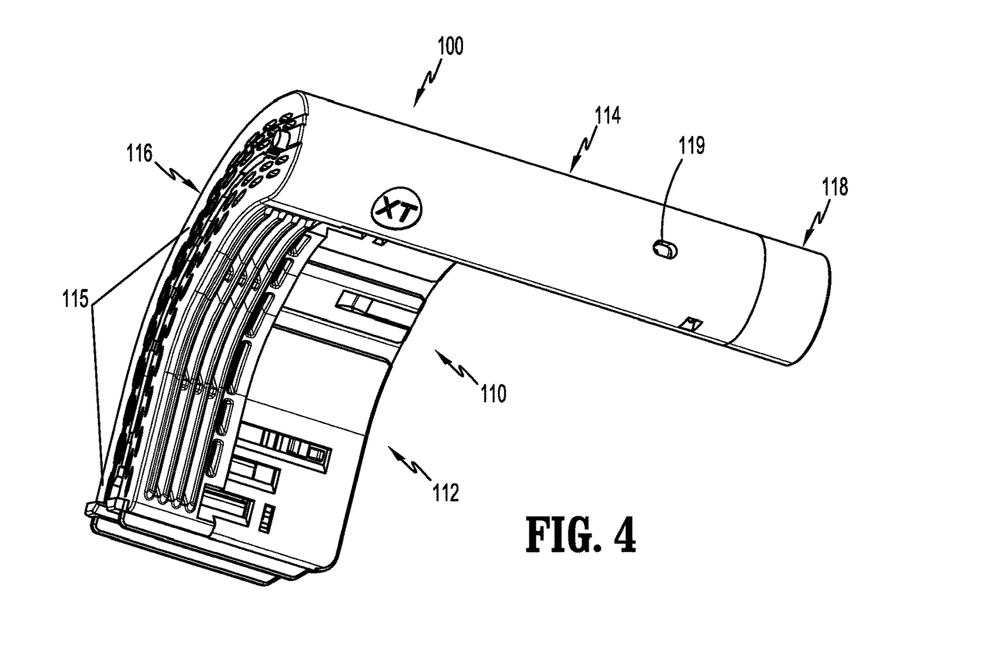
FIG. 4 is a side perspective view of the replaceable cartridge assembly shown in FIG. 2 without the shipping cap.
Figure 5:
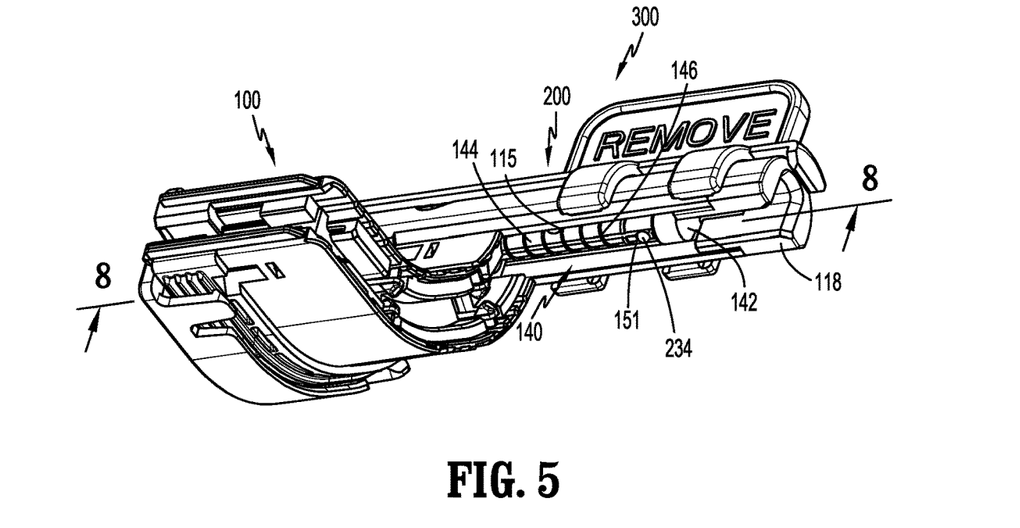
FIG. 5 is a bottom perspective view of the replaceable cartridge assembly and shipping cap shown in FIG. 3 with the shipping cap attached to the replaceable cartridge assembly.

The staple retaining portion 220 of the shipping cap 200 includes a staple retaining surface 222 configured to be disposed adjacent a plurality of staple receiving pockets 115 (FIG. 4) of the staple cartridge 116. The staple retaining surface 222 ensures staples (not shown) supported within the staple cartridge 116 of the replaceable cartridge assembly 100 remain within the plurality of staple receiving pockets 115 of the staple cartridge 116 during shipping of the reload assembly 300, and prior to the shipping cap 200 being separated from the replaceable cartridge assembly 100. First and second pairs of clips 224, 226 extend from the staple retaining portion 220 of the shipping cap 200 and form a snap fit engagement between the base portion 112 of the housing 110 of the replaceable cartridge assembly 100 and the staple retaining portion 220, FIGS. 4 and 5 illustrate the replaceable cartridge assembly 100 with (FIG. 5) and without (FIG. 4) the shipping cap 200 attached. The replaceable cartridge assembly 100 will only be described to the extent necessary to fully disclose the aspects of the disclosure. For a detailed description of the structure and operation of an exemplary internal components of a cartridge assembly, e.g., a pusher assembly, please refer to the '544 publication.

As noted above, the housing 110 of the replaceable cartridge assembly 100 includes the base portion 112 and the alignment, pin retaining portion 114. The alignment pin retaining portion 114 defines a longitudinal channel 115 (FIG. 5) for operably receiving the alignment pin assembly 140 (FIG. 5). The alignment pin assembly 140 is maintained within the alignment pin retaining portion 114 by an end cap 118. A proximal portion of the alignment pin retaining portion 114 defines a recess or relief 117 (FIG. 10) that permits releasable engagement between the alignment pin assembly 140 and the abutment member 44 of the deployment member 40 (FIG. 3). The alignment pin retaining portion 114 further defines an opening 119 (FIG. 4) that is positioned to receive the locking pin 230 of the shipping cap 200 when the shipping cap 200 is attached to the replaceable cartridge assembly 100.

The alignment pin assembly 140 includes a base member 142 and the alignment pin 144. The alignment pin 144 extends from the base member 142 distally towards the anvil assembly 60 (FIG. 2) when the replaceable cartridge assembly 100 is secured to the clamp slide members 30 (FIG. 2) of the end effector 20. Although shown as being separate components, it is envisioned that the base member 142 and the alignment pin 144 may be integrally formed with each other. As described below, the alignment pin 144 of the alignment pin assembly 140 is moveable between a locked or retracted position (FIG. 8) and an unlocked position (FIG. 12) to permit separation of the shipping cap 200 from the replaceable cartridge assembly 100. The alignment pin 144 is further movable from the unlocked position to an advanced position (not shown) in engagement with the anvil assembly 60 to provide alignment between the replaceable cartridge assembly 100 and the anvil assembly 60 during operation of the stapling device 10 (FIG. 1). The alignment pin 144 is biased to the retracted position by a spring 146.

Figure 6:
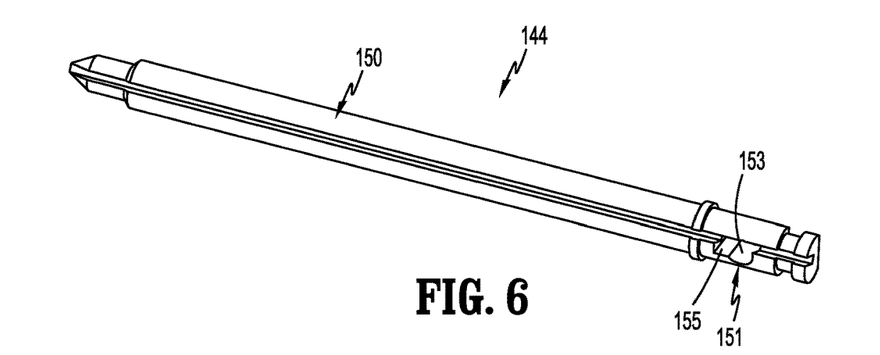
FIG. 6 is a perspective side view of an alignment pin of the replaceable cartridge assembly shown in FIG. 5.
Figure 7:
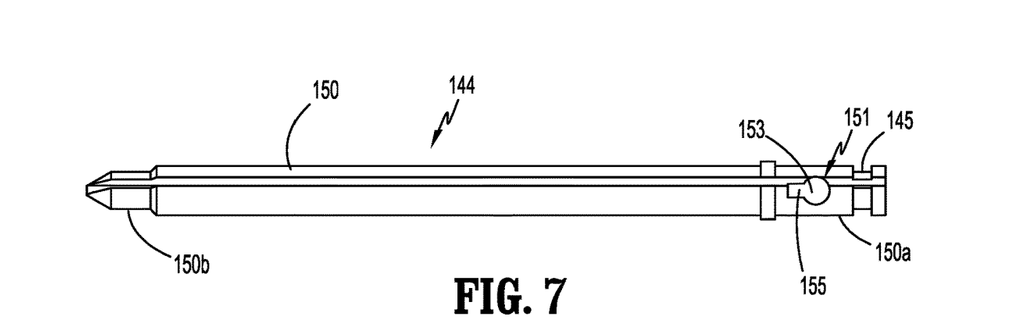
FIG. 7 is a top view of the alignment pin shown in FIG. 6.

FIGS. 6 and 7 illustrate the alignment pin 144 of the alignment pin assembly 140. The alignment pin 144 includes an elongate body 150 having a proximal portion 150a configured for engagement with the base member 142 of the alignment pin assembly 140 and a tapered distal portion 150b configured to facilitate receipt of the alignment pin 144 within an opening (not shown) formed in the anvil assembly 60 (FIG. 2). The proximal portion 150a of the alignment pin 144 may include one or more notches 145, or be otherwise configured to facilitate secure engagement of the alignment pin 144 with the base member 142 (FIG. 5). The proximal portion 150a of the alignment pin 144 may be secured to the base member 142 by friction fit, adhesive, welding, or in any other suitable manner.

The elongate body 150 of the alignment pin 144 defines a key hole slot 151. The key hole slot 151 includes a first portion 153 and a second portion 155 in communication with the first portion 153. The first portion 153 of the key hole slot 151 is sized and dimensioned to receive the head portion 234 of the locking pin 230 of the shipping cap 200. The second portion 155 of the key hole slot 151 is sized and dimensioned to receive at least a portion of the shaft portion 232 of the locking pin 230. As shown, the first portion 153 is circular and the second portion is rectangular, however, the first and second portions 153, 155 may be of any shape. The key hole slot 151 is positioned on the elongate body 150 of the alignment pin 144 such that the first portion 153 of the key hole slot 151 aligns with the opening 119 (FIG. 4) in the alignment pin retaining portion 114 of the housing 112 of the replaceable cartridge assembly 100 when the alignment pin 144 is in the locked position and the second portion 155 aligns with the opening 119 when the alignment pin 144 is in the unlocked position.

Figure 8:
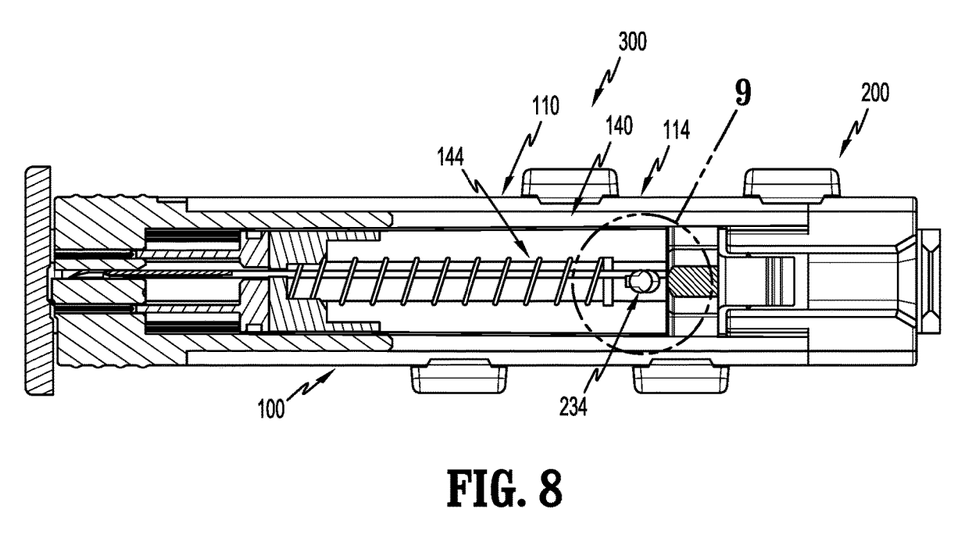
FIG. 8 is a cross-sectional view taken along section line 8-8 of FIG. 5.
Figure 9:
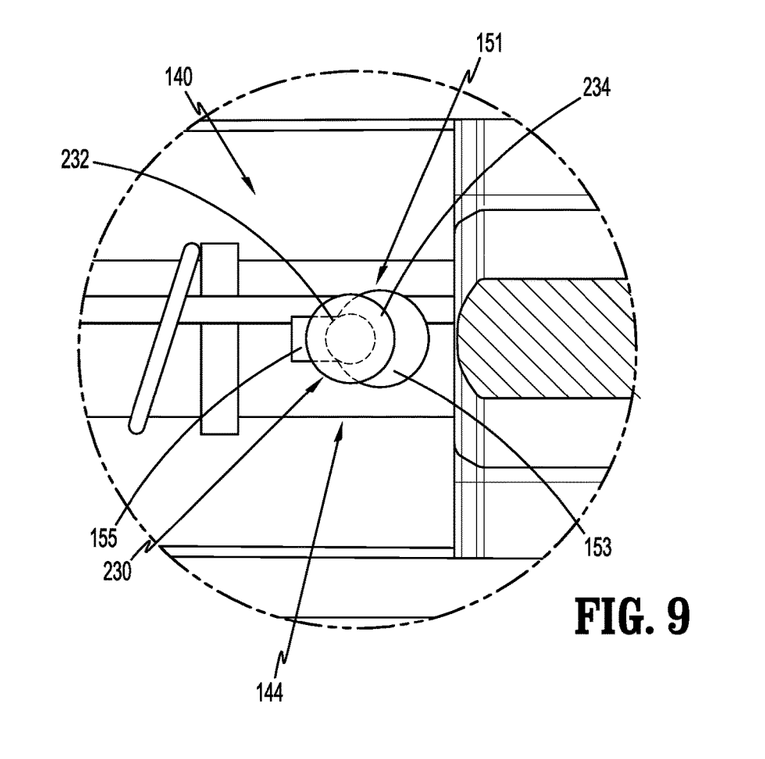
FIG. 9 is an enlarged view of the indicated area of detail shown in FIG. 8.

FIGS. 8 and 9 illustrate the reload assembly 300 including the shipping cap 200 attached to the replaceable cartridge assembly 100 with the alignment pin 144 of the alignment pin assembly 140 in the locked or retracted position to prevent separation of the shipping cap 200 from the replaceable cartridge assembly 100. When the shipping cap 200 is attached to the replaceable cartridge assembly 100, the locking pin 230 is received through the opening 119 (FIG. 4) in the alignment pin retaining portion 114 of the housing 110 of the replaceable cartridge assembly 100 and through the key hole slot 151 in the elongate body 150 of the alignment pin 144. When the alignment pin 144 is in the locked or retracted position, the shaft portion 232 of the locking pin 230 of the shipping cap 200 is received within the second portion 153 of the key hole slot 151. In this manner, the head portion 234 of the locking pin 232 engages the body portion 150 of the alignment pin 144, thereby preventing the locking pin 230 from being withdrawn through the key hole slot 151, thus locking the shipping cap 200 to the replaceable cartridge assembly.

Figure 10:
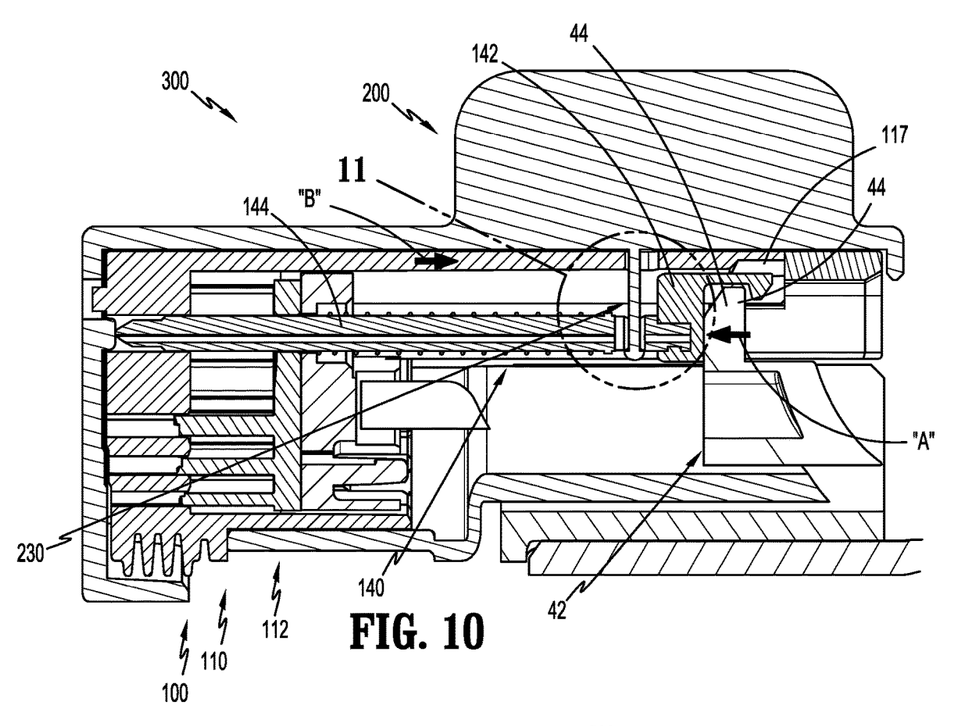
FIG. 10 is a cross-sectional side view taken along section line 10-10 of FIG. 1, with the alignment pin in an unlocked position.
Figure 11:
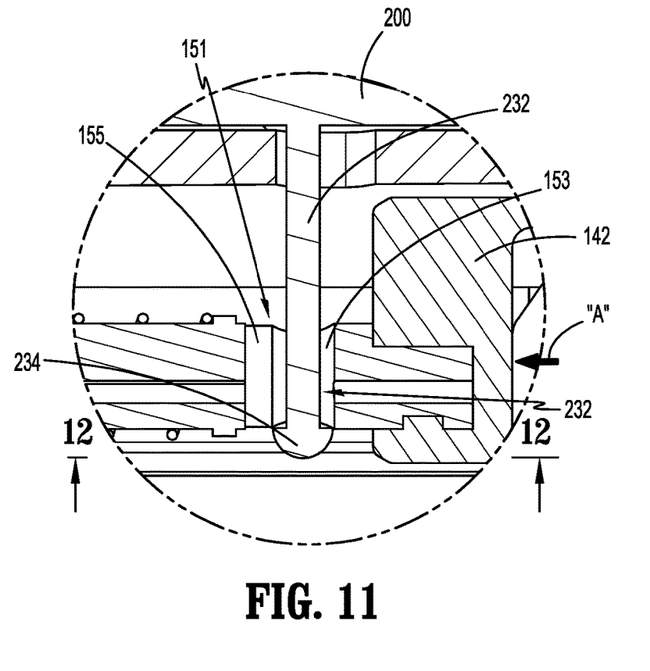
FIG. 11 is an enlarged view of the indicated area of detail shown in FIG. 10.
Figure 12:
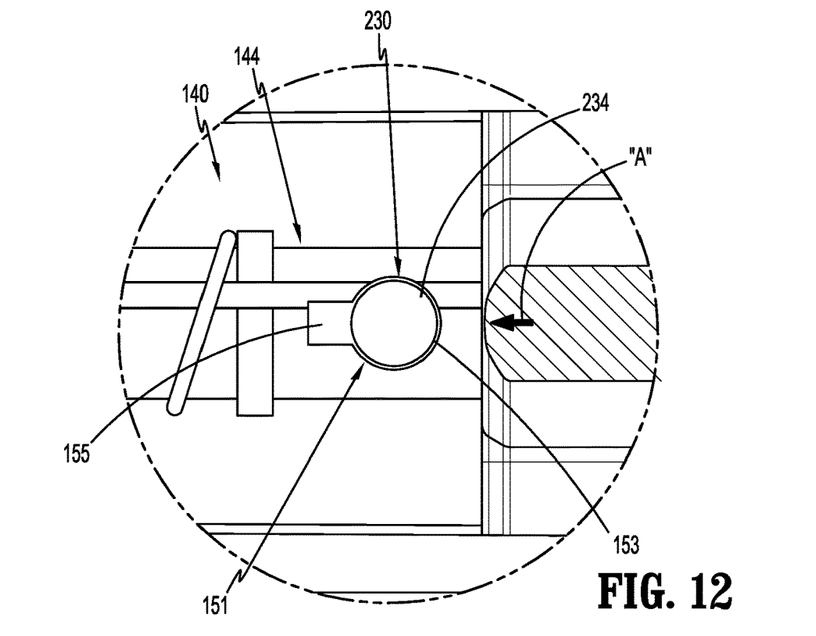
FIG. 12 is an enlarged view of the indicated area of detail shown in FIG. 11.

FIGS. 10-12 illustrate the reload assembly 300 including the shipping cap 200 attached to the replaceable cartridge assembly 100 with the alignment pin 144 of the alignment pin assembly 140 in the unlocked position to permit separation of the shipping cap 200 from the replaceable cartridge assembly 100. When the alignment pin 144 is in the unlocked position, the shaft portion 232 of the locking pin 230 of the shipping cap 200 is received within the first portion 153 of the key hole slot 151 such that the head portion 234 of the locking pin 230 is aligned with the first portion 153. In this manner, the locking pin 230 is free to be withdrawn through the first portion of the key hole slot 151, thereby permitting separation of the shipping cap 200 from the replaceable cartridge assembly 100.

The alignment pin 144 of the alignment pin assembly 140 is moved against the bias of spring 146 to the unlocked position, as indicated by arrow "A" in FIGS. 10-12, as the replaceable cartridge assembly 100 of the reload assembly 300 is loaded into to the end effector 20 (FIG. 1) of the stapling device 10. More particularly, loading the replaceable cartridge assembly 100 into the end effector 20 includes aligning the body portion 112 of the housing 110 of the replaceable cartridge assembly 100 with the channel 31 (FIG. 2) between the head portion 32 of the clamp slide members 30 and moving the replaceable cartridge assembly 100 proximally within channel 31, as indicated by arrow "B" in FIG. 10. As the replaceable cartridge assembly 100 is moved proximally, the abutment portion 44 of the deployment member 42 engages the base member 142 of the alignment pin assembly 140, causing the alignment pin 144 to move relative to the housing 110 of replaceable cartridge assembly 100 thereby unlocking the shipping assembly 200 from the replaceable cartridge assembly 100.

Figure 13:
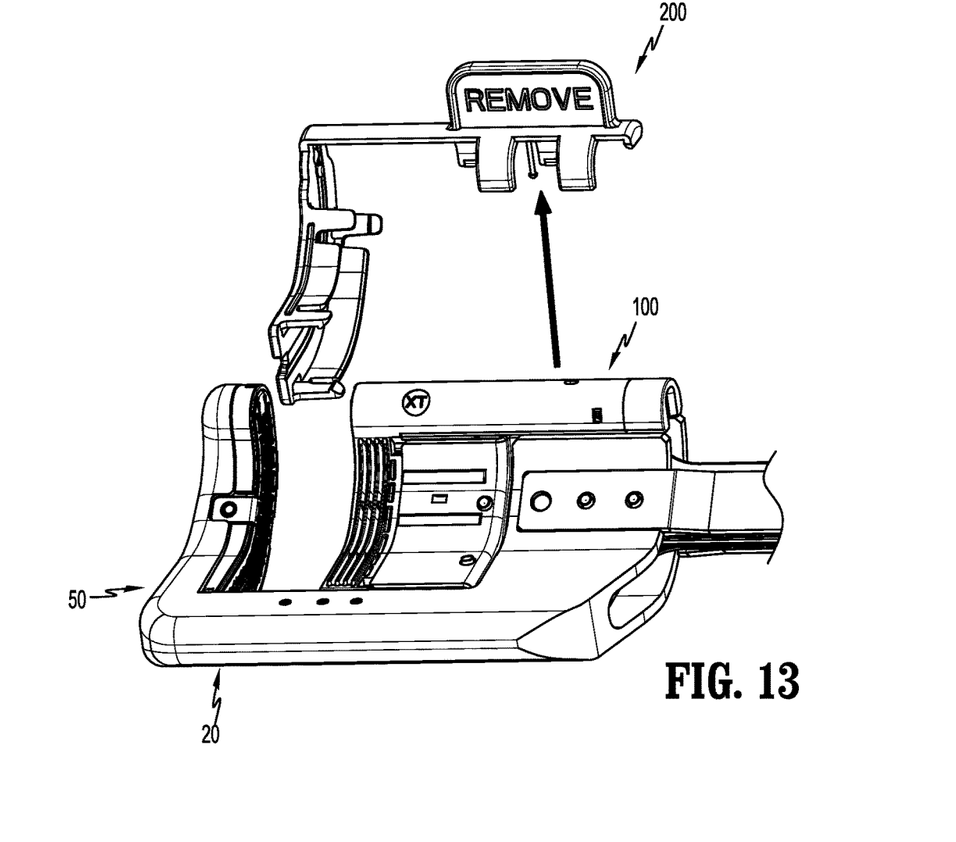
FIG. 13 is a side perspective view of the end effector shown in FIG. 2 with the replaceable cartridge assembly in a loaded position and the shipping cap separated from the replaceable cartridge assembly.

FIG. 13 illustrates the replaceable cartridge assembly 100 secured to the frame assembly 50 of the stapling device 10 (FIG. 1) and the shipping cap 200 being separated from the replaceable cartridge assembly 100 after movement of the alignment pin 144 (FIG. 12) to the unlocked position.

Persons skilled in the art will understand that the devices and methods specifically described herein and illustrated in the accompanying drawings are non-limiting exemplary aspects of the disclosed stapling device. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosed ligation clip. Accordingly, the disclosure is not to be limited by what has been particularly shown and described, except as indicated by the appended claims.

The invention claimed is:
1. A surgical stapling device comprising:
an elongate body portion defining a longitudinal axis, the elongate body portion having a distal portion;
an end effector supported on the distal portion of the elongated body portion, the end effector including:
a housing having a base portion and a jaw portion, the base portion being secured to the distal portion of the elongate body portion;
an anvil assembly supported on the jaw portion;

a cartridge assembly releasably supported on the base portion, the cartridge assembly including a cartridge housing and an alignment pin assembly having an alignment pin received within the cartridge housing, the alignment pin defining a key hole slot and being movable between a locked position and an unlocked position, and between the unlocked position and an advanced position in which the alignment pin extends from the cartridge housing and is engaged with the anvil assembly; and a shipping cap releasably attached to the cartridge assembly, the shipping cap including a locking pin received through the key hole slot, wherein when the alignment pin is in the locked position, the alignment pin prevents separation of the shipping cap from the cartridge assembly and when the alignment pin is in the unlocked position, the alignment pin permits separation of the shipping cap from the cartridge assembly.

2. The surgical stapling device of claim 1, wherein the key hole slot includes a first portion and a second portion, and the locking pin includes a shaft portion and a head portion, the shaft portion being received within the second portion of the key hole slot when the alignment pin is in the locked position and the shaft portion being received within the first portion of the key hole slot when the alignment pin is in the unlocked position.

3. The surgical stapling device of claim 2, wherein the first portion of the key hole slot is circular and the second portion of the key hole slot is rectangular.

4. The surgical stapling device of claim 2, wherein the head portion of the locking pin engages the alignment pin when the alignment pin is in the locked position and is free to pass through the alignment pin when the alignment pin is in the unlocked position.

5. The surgical stapling device of claim 1, further including a deployment member, wherein movement of the deployment member from a first position to a second position moves the alignment pin from the unlocked position to an advanced position in engagement with the anvil assembly.

6. The surgical stapling device of claim 5, further including a body having a stationary handle and a trigger, wherein movement of the trigger towards the stationary handle causes the deployment member to move from the first position to the second position.

7. The surgical stapling device of claim 5, further including at least one thumb button in operable engagement with the deployment member, wherein movement of the at least one thumb button moves the deployment member from the first position to second position.

8. The surgical stapling device of claim 1, wherein shipping cap is in snap fit engagement with the cartridge assembly.

9. The surgical stapling device of claim 1, wherein the shipping cap includes a body portion and a staple retaining portion.

10. The surgical stapling device of claim 1, wherein the alignment pin assembly further includes a spring for biasing the alignment pin to the locked position.

11. A reload assembly comprising:
a cartridge assembly including a housing and an alignment pin assembly having an alignment pin received within the housing, the alignment pin defining a key hole slot and being movable between a locked position and an unlocked position, and movable between the unlocked position and an advanced position in which the alignment pin extends from the housing; and a shipping cap releasably attached to the cartridge assembly, the shipping cap including a locking pin received through the key hole slot, wherein when the alignment pin is in the locked position, the alignment pin prevents separation of the shipping cap from the cartridge assembly and when the alignment pin is in the unlocked position, the alignment pin permits separation of the shipping cap from the cartridge assembly.

12. The reload assembly of claim 11, wherein the key hole slot includes a first portion and a second portion, and the locking pin includes a shaft portion and a head portion, the shaft portion being received within the second portion when the alignment pin is in the locked position and the shaft portion being received within the first portion when the alignment pin is in the unlocked position.

13. The reload assembly of claim 12, wherein the first portion is circular and the second portion is rectangular.

14. The reload assembly of claim 12, wherein the head portion of the locking pin engages the alignment pin when the alignment pin is in the locked position and is free to pass through the alignment pin when the alignment pin is in the unlocked position.

15. The reload assembly of claim 11, wherein shipping cap is in snap fit engagement with the cartridge assembly.

16. The reload assembly of claim 11, wherein the shipping cap includes a body portion and a staple retaining portion.

17. The reload assembly of claim 11, wherein the alignment pin assembly further includes a spring for biasing the alignment pin to the locked position.

\* \* \* \* \*